United States Patent [19]

Bartke

[11] 4,351,801

[45] Sep. 28, 1982

[54] COMBUSTION APPARATUS FOR USE IN ELEMENTARY ANALYSIS

[75] Inventor: Rolf Bartke, Düsseldorf, Fed. Rep. of Germany

[73] Assignee: Antek Instruments GmbH, Düsseldorf, Fed. Rep. of Germany

[21] Appl. No.: 263,582

[22] Filed: May 14, 1981

[30] Foreign Application Priority Data

Apr. 22, 1981 [DE] Fed. Rep. of Germany ....... 3116049

[51] Int. Cl.³ ...................... G01N 25/22; G01N 31/12
[52] U.S. Cl. ................................. 422/78; 23/230 PC
[58] Field of Search ............... 422/78, 80; 23/230 PC; 73/25

[56] References Cited

U.S. PATENT DOCUMENTS

| | | | |
|---|---|---|---|
| 3,188,180 | 6/1965 | Holler | 422/78 X |
| 3,647,385 | 3/1972 | Stephens | 422/78 X |
| 3,898,041 | 8/1975 | Stephens | 422/78 X |
| 4,244,917 | 1/1981 | Woods et al. | 422/78 |

Primary Examiner—Ronald E. Serwin

Attorney, Agent, or Firm—Fitzpatrick, Cella, Harper & Scinto

[57] ABSTRACT

The invention relates to a combustion apparatus for elementary analysis. Solid material samples contained in small tubes are introduced into the combustion apparatus by means of an automatic inserting device. The automatic inserting device is provided with an automatic loading device for the small tubes. In order to keep the dimensions of the combustion apparatus within reasonable limits and nevertheless to permit the largest possible quantities of sample material which are representative for the material to be investigated, the quartz tube serving to burn the sample material and extending through a main combustion zone is of circuitous shape, preferably in the form of a coil. For the purpose of burning liquid samples, use is made of a plug having a through bore, said plug serving to close the receiving aperture of the quartz tube. Said through bore is closed by means of a plastic material which is adapted to be penetrated by an injection needle serving to inject the liquid sample material. Upon the injection needle being withdrawn, the plastic material is adapted again to effect gastight closure of the quartz tube.

10 Claims, 3 Drawing Figures

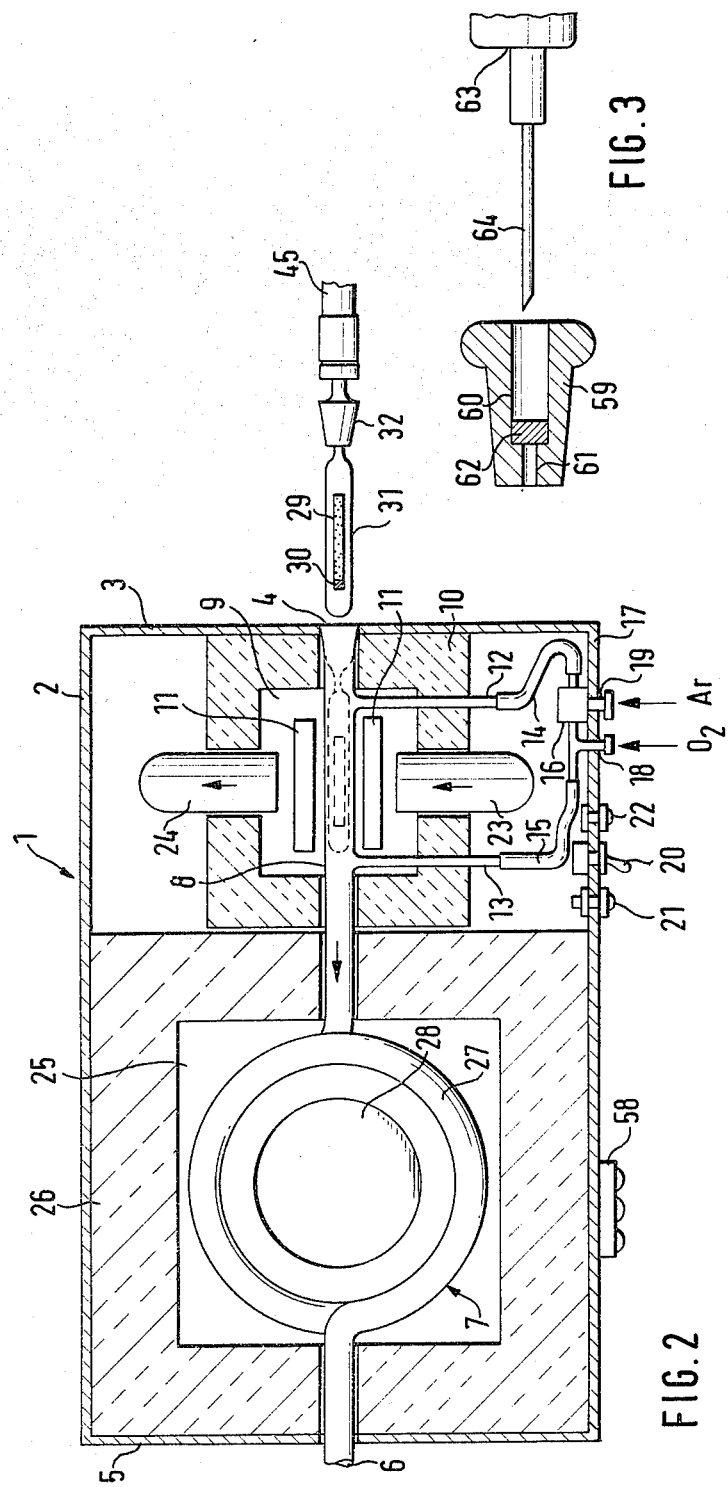

COMBUSTION APPARATUS FOR USE IN ELEMENTARY ANALYSIS

FIELD OF THE INVENTION

The present invention relates to a combustion apparatus for use in elementary analysis, particularly nitrogen analysis, comprising a quartz tube which extends from an inlet aperture for the medium to be analyzed through a digesting zone and a main combustion zone to an outlet aperture, at least one oxygen supply connection with which the section of the quartz tube extending through the digesting zone is connected, a first heating device section designed to permit the heating temperature in the digesting zone to be varied in accordance with a predetermined timing program, a second heating device section serving to heat the main combustion zone and to maintain it at an essentially constant temperature and at least one plug permitting the inlet aperture of the quartz tube to be closed.

DESCRIPTION OF THE PRIOR ART

The gases produced in a combustion apparatus of the aforedescribed type by burning the sample which may be removed through the outlet aperture of the quartz tube can be introduced into a spectrometer permitting the composition of the gases to be determined.

For the purpose of investigating solid samples use is made in a combustion apparatus of the type indicated of a closure plug which is provided with a tray designed to receive the solid sample. In this case, the solid samples to be analyzed are manually introduced into a receiving tray. The introduction of the closure plug together with the receiving tray containing the solid sample into the inlet aperture of the quartz tube is also effected manually.

As regards the known combustion apparatus, the fact should be noted that the section of the quartz tube which extends through the combustion zone is aligned with the section extending through the digesting zone and that the latter therefore has a limited length determined by the size of the apparatus, said length being the same as that of the main combustion zone. In view of this arrangement, the maximum weight of a solid sample to be analyzed amounts to about 100 mg. Should a larger quantity of sample material be introduced into the digesting zone of the quartz tube, it would be necessary to supply a correspondingly larger quantity of oxygen via the oxygen supply connection. This would result in an increase in the flow rate of the oxygen and the gases developed in the quartz tube. Such an increase in the flow rate would, in turn, result in a shortening of the period of time for which the gas developed in the digesting zone and intended to react with the oxygen in the main combustion zone is retained therein. However, any reduction in the dwell time would result in an incomplete reaction between the gas developed in the digesting zone and the oxygen, this, in turn, resulting in an adulteration of the results of the analysis. It is thus evident that the amount of sample material to be employed is limited.

However, where a small quantity of sample material of e.g. 100 mg is employed, the disadvantage frequently results that the sample is not representative of the material to be analyzed from which the sample was taken because the material is not sufficiently homogeneous.

OBJECT OF THE INVENTION

It is an object of this invention to increase the throughput of material to be analyzed per unit time.

SUMMARY OF THE INVENTION

On the basis of a combustion apparatus of the type described in the introduction, the invention, in a first embodiment thereof, provides for the analysis of solid materials an arrangement in which, in a per se known manner, each closure plug is provided with a tray receiving the solid sample, the arrangement being such that introducing the closure plug into the inlet aperture will cause the tray to extend into the section of the quartz tube located in the digesting zone and that an automatic loading device is provided which permits successive or alternating introduction of the closure plugs provided with said receiving trays.

In a modified embodiment of the invention, there may be provided an automatic loading device designed to fill with solid samples the receiving trays provided on the closure plugs.

The employment of the automatic introducing and loading devices is intended to expedite the changing of samples. In addition, the invention provides an embodiment which is adapted to be combined with the first embodiment and which is characterized by the fact that the section of the quartz tube extending through the main combustion zone has the shape of a coil. This permits the employment of larger quantities of sample material because the increased flow rate mentioned earlier is compensated for by a greater length of travel, the gas developed in the digesting zone and the oxygen introduced into the digesting zone being required to flow through the coiled section of the quartz tube in the main combustion zone so that there is no reduction in dwell time and a complete reaction occurs in the main combustion zone.

The section of the quartz tube extending through the main combustion zone may preferably have the shape of a coil or spiral.

The present invention also relates to the analysis of liquid samples with the aid of a combustion apparatus of the type described earlier. In order to permit maximum efficiency to be obtained in using the combustion apparatus, i.e. to provide for minimum intervals of time between the introduction of successive samples, it is proposed according to the invention to employ a closure plug provided with a bore which is closed by means of a plastic material which is adapted to be penetrated by an injection needle serving to inject a liquid sample, said bore being closed by the plastic material in a gastight manner upon the injection needle being withdrawn.

BRIEF DESCRIPTION OF THE DRAWINGS

Other features and advantages of this invention will be apparent from the following detailed description, appended claims and the accompanying drawings.

FIG. 2 is a horizontal cross-sectional view of the combustion apparatus of FIG. 1, the automatic loading device and the automatic introducing device being omitted; and FIG. 3 is a longitudinal cross-section of a closure plug and an injection needle for liquid samples.

DETAILED DESCRIPTION OF PREFERRED EMBODIMENTS

Figure 1:
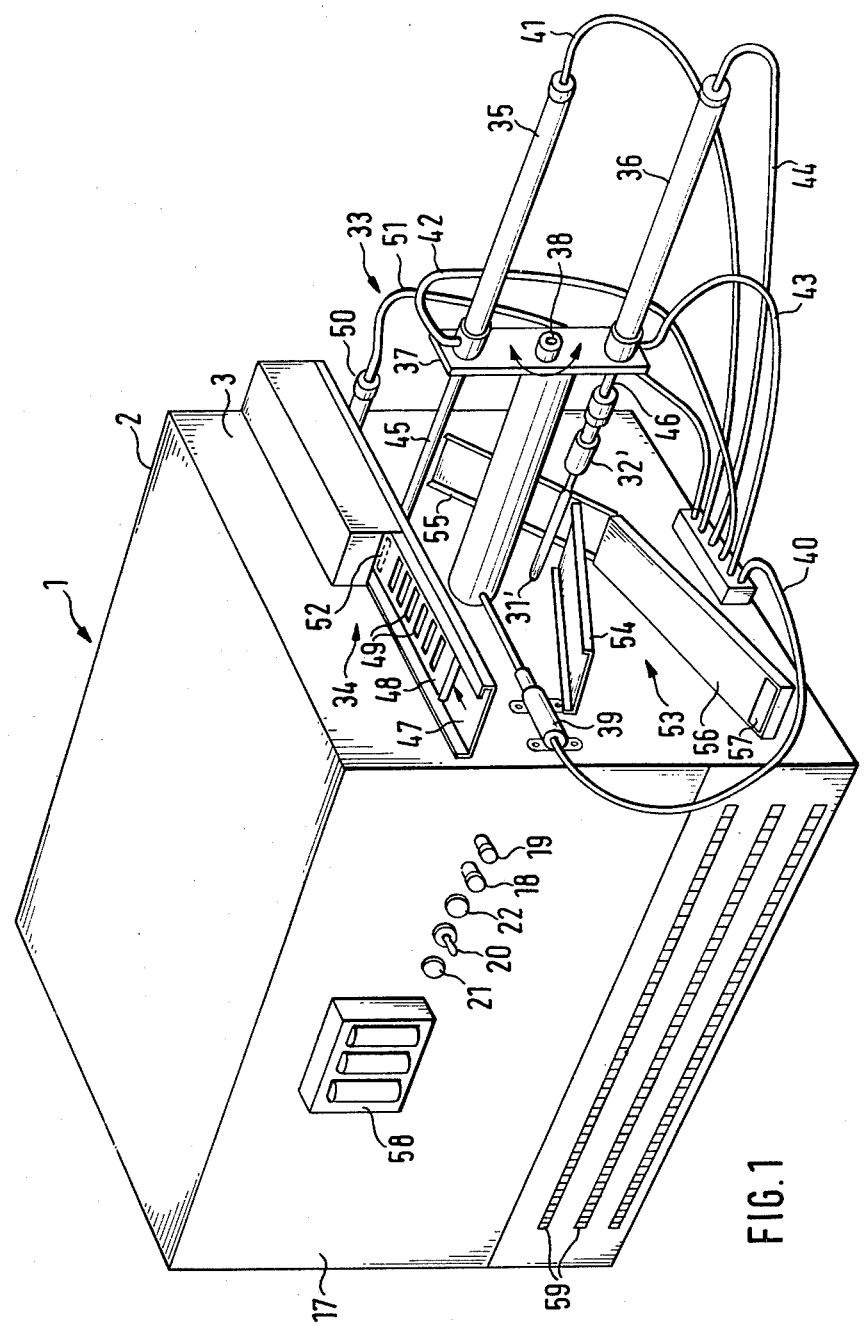
FIG. 1 is an oblique view of a combustion device according to the invention for use with solid material samples.

The combustion apparatus shown in FIGS. 1 and 2 is provided with a housing 2, the side wall 3 of which is provided with a closable aperture 4 serving to introduce the samples to be analyzed. The opposite side wall 5 of the housing is provided with an outlet aperture 6 for the gas produced during combustion of the samples.

As shown in FIG. 2, there extends through the combustion apparatus 1 a quartz tube 7 from the inlet aperture 4 first along a straight tubular section 8 through a so-called digesting zone 9 which is surrounded by heat-insulating material. The digesting zone 9 is adapted to be heated by means of heating elements, preferably so-called quartz bright emitters.

The tubular section 8 of quartz tube 7 extending through the digesting zone 9 is provided with two connecting spigots 12 and 13. The connecting spigot 12 is disposed upstream of the connecting spigot 13 taking into consideration the direction of gas flow. The connecting spigot 13 is connected by a connecting element 15 to a gas supply connection 18 for oxygen provided on the front side 17 of housing 2. Connecting spigot 12 is connected by means of a hose element 14 to a solenoid valve 16. The solenoid valve 16 is also connected to the oxygen supply connection 18 and another supply connection 19 for an inert gas, e.g. argon, provided on the front side 17 of casing 2. A change-over switch 20 also provided on the front side 17 of casing 2 permits solenoid valve 16 to be controlled in such a way that connection spigot 12 is either supplied with oxygen or with the inert gas. Connecting spigot 13 is exclusively fed with oxygen. The two switch positions are indicated by pilot lamps 21 and 22 mounted on front panel 17.

Mounted in the lower part of housing 2 is a blower (not shown). The delivery pipe 23 of the blower is connected to the digesting zone 9. Disposed on the opposite side is a discharge tube 24 for the air supplied by the blower. The air supplied by the blower makes it possible to cool the quartz bright emitters 11 and the straight section 8 of the quartz tube in the digesting zone 9 whenever necessary, particularly before the introduction of a new sample.

Connected to the digesting or opening zone 9 is a main combustion zone 25 which is also surrounded by heat insulating material 26. The section of quartz tube 7 extending through the main combustion zone 25 has the form of a coil 27 comprising a plurality of turns. The main combustion zone 25 is heated by means of a resistance heater 28. Heating of the digesting zone is effected progressively in accordance with an accurately predetermined temperature profile, i.e. in accordance with a predetermined timing schedule. In the main combustion zone, however, the temperature is essentially maintained constant at an elevated level. This arrangement ensures that the sample is gasified within the shortest possible period of time and that it is converted into a gaseous combustion product which is suitable for the subsequent elementary analysis. In the case of nitrogen analysis, for example, this gaseous combustion product is nitrogen monoxyde (NO). In this case, the temperature in the digesting zone is increased, for example, from 100° C. to 900° C. In the main combustion zone a constant temperature between about 1000° C. and 1100° C. is maintained.

What is important is that the gas developed in the digesting zone 9 is allowed sufficient time in the main combustion zone 25 for the gas to react with the oxygen. The reaction time of the gas in the main combustion zone 25 depends on the rate at which the gas flows through quartz tube 7. This, in turn, depends on the quantity of oxygen and inert gas, respectively, introduced via the gas supply spigots 18 and 19. The quantities of oxygen and inert gas, in turn, depend on the weight of the sample. The larger the weight of the sample the greater must be the length of quartz tube 7, i.e. the number of turns forming the coiled quartz tube section 27 in the main combustion zone 25.

The solid samples to be burned are received by small glass tubes 29 which are provided with plugs 30 capable of being removed by melting. Such a plug consists, for example, of paraffin which is liquefied in the digesting zone 9 so as to flow out of the tube. This permits the gas produced from the sample material to flow out of the small glass tube 29.

The small glass tube is introduced into the straight section 8 of quartz tube 7 in the form of a spoon 31 mounted on a plug 32 which latter serves to close the receiving aperture 4. In FIG. 2, a tube 29 is indicated in position in tube section 8 by broken lines. Both the plug 32 and the spoon 31 are made of glass.

In FIG. 1 the combustion apparatus 1 is shown to include an inserting device 33 and a loading device 34. The inserting device comprises two pneumatically operable pushing cylinders 35 and 36 which are mounted on a rotary member 37 which is adapted to be rotated within a range of 180° about a rotary axis 38 in a clockwise or anti-clockwise direction. The rotary member 37 is adapted to be rotated by means of a pneumatic motor 39 adapted to rotate axle 38 through gearing (not shown). Motor 39 is connected to a source of compressed air by a hose 40.

The pushing cylinder 35 is connected to the source of compressed air by means of two hoses 41, 42, the pushing cylinder 36 being connected by means of two hoses 43, 44.

Mounted in the piston rod 45 of pushing cylinder 35 is the plug 32 with the spoon 31 shown in FIG. 2. In FIG. 1 piston rod 45 is shown in its fully extended position which is indicated by broken lines in FIG. 2.

In FIG. 1 the piston rod of pushing cylinder 36 is shown in its fully withdrawn position. In this case, spoon 31' mounted on plug 32' supported by piston rod 46 is in such a position that its aperture is directed downwardly.

The loading device 34 includes a guide plate 47 on which a magazine plate 48 is slidable. The magazine plate 48 is provided with apertures 49 receiving the sample tubes 29. A pneumatic motor 50 permits the magazine plate 48 to be moved in the direction of the arrow. Pneumatic motor 50 is connected to the source of compressed air by means of a hose 51. The magazine plate 48 is driven by pneumatic motor 50 via a rack-and-pinion mechanism (not shown).

The guide plate 47 is provided above the receiving aperture 4 which is now visible in FIG. 1 with a discharge aperture 52 indicated in broken lines. The receiving apertures 49 of the magazine plate 48 and the discharge aperture 52 of guide plate 47 are so dimensioned that they are slightly longer and wider than the tubes 29 so that each tube contained in a receiving aperture 49 will drop through discharge aperture 52 upon the respective receiving aperture 49 being aligned with discharge aperture 52.

Before spoon 31 is introduced into the receiving aperture 4, it is placed into a position of readiness in front of aperture 4 so that it can receive the tube which is dropped through discharge aperture 52. Following this, piston rod 45 is extended so that spoon 31 together with the tube is introduced into the straight section 8 of the quartz tube, the receiving aperture 4 being simultaneously closed by plug 32. After the sample has been burned, piston rod 45 is completely withdrawn. Following this, rotary member 37 is rotated through 180°. This motion will cause the aperture of spoon 31 to be directed downwardly. At the same time, plug 32' carrying spoon 31' is turned upwardly. Finally piston rod 46 is advanced into its position of readiness.

The used tube 29 is dropped from spoon 31 as the spoon is inverted, and the tube will be caught by a device 53 comprising two shutes 54 and 55 forming a V-shaped arrangement. Depending on the direction of rotation of rotary member 37, the used tube will drop either on chute 54 or on chute 55. Chute 54 is connected to chute 55 which, in turn, extends towards a collecting container extending along an inclined plane. The lower end of collecting container 56 is provided with an aperture 57 permitting the used tubes to be removed.

Also mounted on front panel 17 of housing 2 is a flow meter 58 for a number of gases. In addition, front panel 17 is provided with air inlet and outlet slots 59 associated with the blower mentioned earlier.

If it is intended to burn a liquid sample, the receiving aperture 4 of quartz tube 7 may be closed by means of plug 59 shown in FIG. 3. This plug is made of glass and provided with a stepped bore comprising two sections 60 and 61 having different diameters. Bore 60, 61 is closed by means of a so-called septum 62. The liquid sample is initially contained in an injection syringe 63, the injection needle 64 of which may be caused to penetrate septum 62. The liquid sample is injected into section 8 of quartz tube 7. Septum 62 consists of a plastic material which is adapted to close bore section 61 in a gastight manner upon injection needle 64 being withdrawn.

Control of the automatic introducing device, the automatic loading device, the timed heating and cooling of the digesting zone, etc. is effected by means of an electronic control unit comprising a microprocessor; this control system is not shown since it does not constitute an object of the invention.

We claim:

1. A combustion apparatus for elementary analysis, particularly for nitrogen analysis, comprising a quartz tube extending from a receiving aperture for the medium to be analyzed through a digesting zone and a main combustion zone up to a discharge aperture, further comprising at least one oxygen supply connection with which the section of the quartz tube extending through the digesting zone is connected, a first heating device section adapted to permit the heating temperature in the digesting zone to be varied in accordance with a predetermined timing program, a second heating device section adapted to heat the main combustion zone and to keep it at an essentially constant temperature and a closure plug for the receiving aperture of said quartz tube, characterized in that, for use in the analysis of solid samples, each closure plug is provided, in a per se known manner, with a tray adapted to receive a solid sample, said receiving tray extending into the section of the quartz tube which is located in said digesting zone upon said plug being introduced into the receiving aperture, and that there is provided an automatic introducing device adapted successively or alternately to introduce said closure plugs, each of which is provided with a receiving tray.

2. The combustion apparatus of claim 1 characterized in that there is provided an automatic loading device adapted to introduce solid material samples into the receiving trays with which said closure plugs are provided.

3. The combustion apparatus of claim 1 characterized in that said automatic introducing device comprises a rotary member provided with at least two pushing cylinders, that said rotary member is adapted to be rotated about an axle extending parallel to the section of the quartz tube which is located in said digesting zone, that the piston rod of each pushing cylinder extends parallel to said axle, that the end of each piston rod extending from its associated pushing cylinder is provided with a closure plug carrying a receiving tray, and that each pushing cylinder is adapted to be aligned with the section of the quartz tube located in said digesting zone by suitable rotation of said rotary member.

4. The combustion apparatus of claim 2 characterized in that said solid material samples are contained in sample containers, e.g. boats or tubes, which are provided with closure means consisting of a material adapted to be melted by heating, and that said loading device is provided with a slidable magazine disposed above the receiving aperture of the quartz tube, said magazine being adapted to be moved transversely of said axle of said rotary member, said sample containers being disposed in said magazine in a side by side arrangement and extending parallel to said axle so as to be adapted to be successively transferred from the magazine in a receiving tray assuming a position of readiness in front of said receiving aperture of the quartz tube, said receiving tray being supported in position by its associated pushing cylinder.

5. The combustion apparatus of claim 4, characterized in that said magazine comprises a magazine plate which is provided with slot-shaped receiving apertures for said sample containers, the width of said slot-shaped apertures being larger than the diameter of the sample containers, and that said magazine plate is slidably supported by a guide plate which is provided with a single slot-shaped discharge aperture for a single sample container, said discharge aperture being disposed above the receiving aperture of the quartz tube.

6. The combustion apparatus of claim 3, characterized in that there is provided a receiving device for the empty sample containers discharged upon the respective receiving tray being inverted, said receiving device being disposed below the rotary path of the receiving trays carried by the piston rods of said pushing cylinders, said path being defined by the rotation of said rotary member.

7. The combustion apparatus of claim 6, characterized in that said rotary member is provided with two pushing cylinders, that said rotary member is adapted to be alternatingly rotated through 180° in opposite directions, that said receiving device comprises two shutes forming an essentially V-shaped arrangement, and that the discharge ends of said shutes are connected to a collecting container.

8. A combustion apparatus for elementary analysis, particularly for nitrogen analysis, comprising a quartz tube extending from a receiving aperture for the medium to be analyzed through a digesting zone and a main combustion zone up to a discharge aperture, further comprising at least one oxygen supply connection with which the section of the quartz tube extending through the digesting zone is connected, a first heating device section adapted to permit the heating temperature in the digesting zone to be varied in accordance with a predetermined timing program, a second heating device section adapted to heat the main combustion zone and to keep it at an essentially constant temperature and at least one closure plug for the receiving aperture of said quartz tube, characterized in that the section of the quartz tube extending through the main combustion zone is of coiled shape.

9. The combustion apparatus of claim 8, characterized in that the section of the quartz tube extending through the main combustion zone has the shape of a coil or spiral.

10. A combustion apparatus for elementary analysis, particularly for nitrogen analysis, comprising a quartz tube extending from a receiving aperture for the medium to be analyzed through a digesting zone and a main combustion zone up to a discharge aperture, further comprising at least one oxygen supply connection with which the section of the quartz tube extending through the digesting zone is connected, a first heating device section adapted to permit the heating temperature in the digesting zone to be varied in accordance with a predetermined timing program, a second heating device section adapted to heat the main combustion zone and to keep it at an essentially constant temperature and at least one closure plug for the receiving aperture of said quartz tube, characterized in that for the purpose of closing the receiving aperture of the quartz tube in cases in which it is intended to analyze liquid samples there is provided a closure plug having a through bore which is closed by means of a plastic material which is adapted to be penetrated by an injection needle for injecting a liquid sample into the quartz tube, said through bore being reclosed in a gastight manner by said plastic material upon the injection being withdrawn.

* * * * *